(12) United States Patent
Franssen et al.

(10) Patent No.: US 7,006,213 B2
(45) Date of Patent: Feb. 28, 2006

(54) METHOD FOR INSPECTING THE SURFACE OF A ROLL CYLINDER AND DEVICE THEREFOR

(75) Inventors: Roger Franssen, Montzen-Plombieres (BE); Marc Schyns, Roclenge-sur-Geer (BE); Hugo Uijtdebroeks, Hasselt (BE)

(73) Assignee: Centre de Recherches Metallurgiques, A.S.B.L., Brussels (BE)

( * ) Notice: Subject to any disclaimer, the term of this patent is extended or adjusted under 35 U.S.C. 154(b) by 285 days.

(21) Appl. No.: 10/344,688

(22) PCT Filed: Apr. 23, 2002

(86) PCT No.: PCT/BE02/00060

§ 371 (c)(1),
(2), (4) Date: Feb. 21, 2003

(87) PCT Pub. No.: WO03/008951

PCT Pub. Date: Jan. 30, 2003

(65) Prior Publication Data

US 2004/0022430 A1 Feb. 5, 2004

(30) Foreign Application Priority Data

Jul. 17, 2001 (BE) .................................. 2001/0482

(51) Int. Cl.
*G01N 21/00* (2006.01)
*G01V 8/00* (2006.01)
*B21B 28/02* (2006.01)
*G01B 21/20* (2006.01)

(52) U.S. Cl. ............................. 356/237.2; 250/559.23; 72/236; 33/551

(58) Field of Classification Search .. 356/237.1–237.3, 356/241.1, 241, 241.2; 250/559.06, 559.23, 250/559.42, 571–572, 239, 226; 72/236; 33/551
See application file for complete search history.

(56) References Cited

U.S. PATENT DOCUMENTS 4,226,539 A * 10/1980 Nakagawa et al. .......... 356/445

(Continued)

FOREIGN PATENT DOCUMENTS

DE 3219480 A1 * 5/1982

(Continued)

OTHER PUBLICATIONS

Bahners et al, Technisches Messen TM, vol. 64, No. 9, Sep. 1, 1997, Optische Profilometer Zur . . . , pp. 316-324.

*Primary Examiner*—Gregory J. Toatley, Jr.
*Assistant Examiner*—Sang H. Nguyen
(74) *Attorney, Agent, or Firm*—Jacobson Holman PLLC

(57) ABSTRACT

In a process for the inspection of the surface of a cylindrical body and more especially that of a mill roll, at least one zone of the surface is observed by means of an inspection device having an optical axis oriented towards this zone of the surface with a view to determining the state of the surface. To this end, at least one image of the zone supplied by the inspection device is captured, at least one of the images captured is analysed, the analysis of the image or images captured is compared with the analysis of a reference image, the differences between the analysis of the image or images captured and the analysis of the reference image are detected, and at least the orientation of the optical axis is adjusted so as at least to reduce and preferably to eliminate the differences found.

The device can include mechanical and/or optical means of adjusting the orientation of the optical axis.

8 Claims, 3 Drawing Sheets

U.S. PATENT DOCUMENTS 5,331,178 A * 7/1994 Fukuda et al. ......... 250/559.08
5,469,743 A * 11/1995 Zorn ........................... 73/627
5,652,432 A * 7/1997 Yaginuma ............... 250/559.06
5,763,786 A * 6/1998 Camplin et al. ............... 73/643
5,905,595 A * 5/1999 Minami ..................... 359/618

FOREIGN PATENT DOCUMENTS

| DE | 4130217 | 3/1992 |
| EP | 0697591 | 2/1996 |
| JP | 59174204 A * | 10/1984 |
| JP | 01295108 A * | 11/1989 |
| JP | 08068759 A * | 3/1996 |

* cited by examiner

METHOD FOR INSPECTING THE SURFACE OF A ROLL CYLINDER AND DEVICE THEREFOR

This is a nationalization of PCT/BE02/00060 filed Apr. 23, 2002 and published in French.

BACKGROUND OF THE INVENTION

1. Field of the Invention

The present invention concerns a process for the inspection of the surface of a mill roll, and more generally of a cylindrical body. It likewise relates to a device for implementing this process.

2. Description of the Related Art

There are numerous applications in the industry in which the condition of the surface of a manufacturing tool at least partially determines the quality of the manufactured product. One extremely important particular instance is that of the manufacture of steel strips, the surface finish of which depends to a large extend on the condition of the surface of the working rolls of the rolling mill.

In the course of rolling, in fact, the surface of the working rolls progressively deteriorates due to oxidation, incrustation of oxide particles, cracking caused by thermal shocks or indeed tearing of metal films under the effect of superficial stresses. It is therefore important to inspect the surface of mill rolls regularly, especially the surface of the lower working rolls of the first finishing stands, which wear particularly rapidly.

Initially, inspection of the surface of the rolls consisted in a simple visual examination by an operator when it came to replacing the working rolls. In certain cases, intermediate inspections were required, owing to the presence of defects in the rolled strips for example. It was then necessary to stop the rolling mill and sometimes even to remove the rolls. These intermediate unscheduled stops take a lot of time and entail a loss of productivity. Apart from this disadvantage, the subjective nature of such visual inspections can affect the quality of the examination, which consequently no longer meets current requirements of reliability, reproducibility and rapidity.

Processes and devices for inspecting the surface of mill rolls are of course already known in the prior art, in particular by means of cameras equipped with illumination means and arranged close to the rolls to be inspected. Generally speaking, however, the known systems have the disadvantage of inspecting the surface in a fixed direction.

For the inspection of a surface to be satisfactorily carried out, it should ideally be performed in a specular manner, i.e. that the direction of inspection should be perpendicular to the surface at the point of observation. In the case of surfaces such as those of mill rolls, inspection in a fixed direction rapidly loses any possible specular feature that it might initially have had as the diameter of the rolls decreases due to the straightening operations on the surface of the roll, which are intended to eliminate the defects that have appeared at their surface.

SUMMARY OF THE INVENTION

The present invention aims to solve this disadvantage by proposing a process for improving the inspection of the surface of a mill roll, which takes into account the diameter of this roll and which allows to maintain specular inspection over the entire range of variation of the diameter of the roll. To this end, the invention proposes a process that allows to adjust relative the inclination of the optical axis of the inspection system in relation to the normal to the surface of the roll at the point of observation, and consequently to take account of a modification in the diameter when a roll is changed. Such a change of roll usually takes place several times a day, and the diameter of the new roll put in place is generally different from that of the roll that has been replaced. There is currently a need to be able to adapt the orientation of the inspection system as a function of the diameter of the roll.

In accordance with the present invention, a process for the inspection of the surface of a mill roll, in which at least one zone of said surface is observed by means of an inspection device having an optical axis oriented towards said zone of the surface with a view to determining the state of the surface of said roll, is characterised in that at least one image of said zone supplied by said inspection device is captured, in that at least one of said captured images is analysed, in that the analysis of said captured image or images is compared with the analysis of a reference image, in that the differences between the analysis of the image or of said images captured and the analysis of said reference image are detected, and in that at least the orientation of said optical axis is adjusted so as at least to reduce and preferably to eliminate said differences.

Within this context, the image of the observed zone captured by the inspection device can be analysed by any appropriate method with a view to comparing it with a reference image.

According to one particular embodiment, the orientation of the optical axis of the inspection device directed towards the zone of the surface to be inspected is progressively varied, said zone is observed for each position of said optical axis by scanning parallel to the direction of the axis of the roll, an image of said zone constituted by lines parallel to the direction of the axis of the roll is formed, the average value of the grey level of each of said lines of the image is determined, a profile of said average grey levels is drawn, each of said profiles thus drawn is compared with a reference profile corresponding to a correct inclination of the optical axis, and the inclination of the optical axis is modified in order to correct any differences observed between said profiles thus drawn and said reference profile.

According to a preferred embodiment, the orientation of the optical axis of the inspection device directed towards the zone of the surface to be inspected is progressively varied, said zone is observed for each position of said optical axis by scanning parallel to the direction of the axis of the roll, an image of said zone constituted by lines parallel to the direction of the axis of the roll is formed, the average value of the grey level of each of said lines of the image is determined, a profile of said average grey levels is drawn, the position of a characteristic size of the profile corresponding to each image is determined, and the inclination of the optical axis is adjusted to the position in which the position of said characteristic size of said profile is equal to or close to the characteristic size corresponding to an image for which the reflection is specular at the centre of the image.

In the sense of the present application, said profile is preferably transverse, i.e. drawn in a direction perpendicular to the scanning direction of the image.

The characteristic size of said profile can advantageously be the value of the maximum or the centre of gravity of this profile, for example.

According to an additional feature, the average grey level of a line of the image is determined by measuring the grey level at a predetermined number of points, preferably at each of the points of the line, and by calculating the average value of the grey levels measured at these points of the line.

The grey level at one point is advantageously measured with reference to a predetermined scale, for example a scale including 256 grey levels between absolute black and absolute white, also referred to as white saturation.

The highest grey level is considered to be corresponding to the specular reflection of the inspection light beam, the position of the characteristic size in the profile of the average grey level will indicate the inclination of the optical axis that corresponds best to this specular reflection, and consequently also to the position of the point of specular reflection in the zone observed.

The inclination of the optical axis can be adjusted by any appropriate method.

According to a first possibility, the inclination of the optical axis can be adjusted by mechanical means by pivoting the inspection device or a part of the latter about an axis parallel to the axis of the roll to be observed.

Another possibility consists in adjusting this inclination by optical means. In particular, the light beam of the inspection device or of the camera can be diverted by a mobile system, a set of mirrors or prisms for example, allowing the inclination of the outgoing light beam to be modified.

Of course, the inclination of the optical axis can be manually adjusted on the basis of the results of the image analysis explained above. The adjustment of the inclination of the optical axis can also be advantageously performed automatically, on the basis of the analysis of the images of the zone observed.

So far, reference has been made to a surface inspection performed by specular reflection, i.e. perpendicularly to the surface at the observation point. This is, of course, an ideal situation, in which the optical axis of the inspection device coincides with the normal to the surface at the point of observation. In practice, the reflection may still be considered to be specular if the two above-mentioned directions are at a very small angle to each other, typically less than 0.250 for rolls with a diameter of the order of 750 mm. If this angle increases, the reflection becomes diffuse, this being translated into a large reduction in the illumination of the detector of the inspection device. Observation by diffuse reflection can nevertheless supply interesting information, by improving, for example, the visibility of certain details such as surface defects.

Obtaining an image that can be used in the above-mentioned process requires that several conditions be met in addition to the correct orientation of the observation axis. These are, in particular, the illumination of the zone observed and the sharpness of the image obtained in this zone.

According to a second aspect, the invention relates to a device for the inspection of the surface of a cylindrical body and more especially of a mill roll, which includes means for adjusting the inclination of the optical axis and which can advantageously also include means for adjusting the focusing of the inspection device and means of adjusting the illumination of the zone observed and the sensitivity of the inspection device.

The means for adjusting the inclination of the optical axis can be purely mechanical, i.e. means that ensure simple pivoting of this optical axis about an axis parallel to the axis of the roll.

Owing to the ambient conditions in a rolling mill stand, the inspection device, generally a camera, is housed in a sealed and possibly water-cooled housing. This housing is usually mounted on a transverse rail, i.e. parallel to the axis of the roll.

In order to ensure the pivoting of the optical axis of the inspection device, this device may, according to the invention, include the following elements, separately or in combination:

a fixed housing and means for pivoting the camera within the fixed housing;

a pivoting housing, a camera fixed in said housing, and means for pivoting said housing—together with the camera—relative to the support of the housing;

a housing fixed on a pivoting support, a camera fixed in said housing, and means for pivoting said support.

In particular, the camera can pivot in a housing which can itself pivot, the pivoting of the housing ensuring, for example, a relatively coarse initial adjustment and the pivoting of the camera ensuring the precise final adjustment.

The various pivoting movements mentioned can be achieved by means of appropriate devices, especially pneumatic cylinders mounted between a fixed point and the member (housing, camera, support) to be pivoted.

Advantageously, means for measuring and displaying the inclination of the optical axis of the inspection device, especially of the camera or of the housing and/or of its support, are also provided.

In another variant, the means for adjusting the inclination of the optical axis are optical means or a combination of optical and mechanical means, the mechanical means being reserved for coarse adjustment and the optical means for precise adjustment, for example.

In this variant, the entire inspection device, i.e. the support of the housing, the housing itself and the camera are fixed.

In the present case, the inspection device includes an adjustable optical system, constituted by a set of mirrors and/or movable prisms, arranged in the path of the light beam. The displacement of this optical system, by translation or by rotation, allows to modify the inclination of the light beam emerging from the camera. The position of this optical system and hence the orientation of the outgoing light beam is located by appropriate means known in the prior art.

According to an additional characteristic, the inspection device includes means for adjusting the focusing of the camera in such a way as to obtain sharp images, whatever the diameter of the roll. This adjustment can be performed immediately after the changing of the roll, for example.

The focusing can be adjusted by displacing the inspection device or camera in translation along its optical axis. To this end, the device can be provided with a mechanism, e.g. a pneumatic cylinder or a threaded bar, which ensures parallel displacement of the inspection device or camera, within its housing where relevant.

In another embodiment, the camera can be provided with a lens equipped with an automatic focusing device.

The adjustment of focusing can be manually or advantageously automatically controlled on the basis of the analysis of the images of the zone observed.

The inspection device or camera can also be advantageously fitted with a device for adjusting the power of illumination associated with a device for adjusting the sensitivity of the camera.

In the frequent case of stroboscopic illumination, the range within which the energy of each light pulse can be modified is in fact generally insufficient to enable the system to be used both for specular reflection and for diffuse reflection. Moreover, remaining within the context of stroboscopic illumination, the circuits for automatic monitoring of the gain of the camera do not correctly function when the repetition rate of the illumination pulses is low.

Consequently, the inspection device of the invention is preferably fitted with a camera including a system for remote monitoring of the gain, which is moreover known in the prior art. This monitoring can furthermore be manually performed by an operator or automatically on the basis of the analysis of the grey levels of the images of the zone observed.

BRIEF DESCRIPTION OF THE DRAWINGS

The invention will now be described in greater detail with embodiment examples, which are diagrammatically illustrated by the attached drawings, in which.

It goes without saying that these illustrations only include the elements required to understand the invention. Identical or similar elements are designated by the same reference numerals in the various figures.

DETAILED DESCRIPTION OF THE INVENTION

Figure 1:
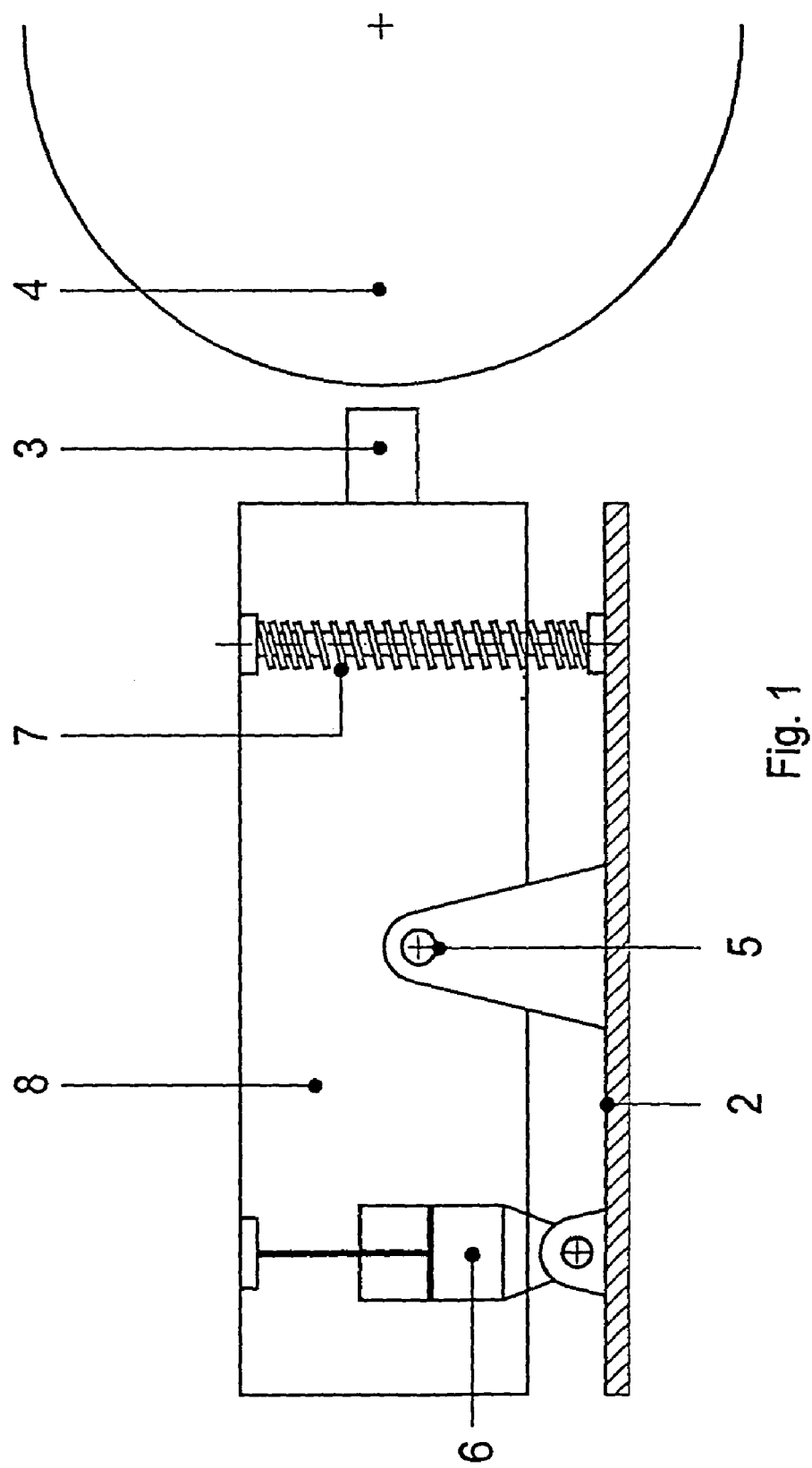
FIG. 1 represents an elevational view of an embodiment of a mechanical device for adjusting the inclination of the optical axis of an inspection device.

A mechanical device for adjusting the inclination of the optical axis of an inspection device has been diagrammatically represented in FIG. 1.

The inspection device, represented here taken as a whole by the protection housing 8, is mounted on a fixed support 2 forming part of a rolling mill stand. Its aiming cap 3 is directed towards a mill roll 4; this is, for example, a lower roll of a hot-rolling finishing stand.

In this embodiment, the inspection device is mounted on the fixed support 2 by way of bearings 5, only one of which is visible in the figure, in such a way as to be able to pivot about an axis parallel to the axis of the roll 4. The pivoting movement of the inspection device is applied by means of a pneumatic cylinder 6 arranged between the fixed support 2 and the inspection device 1, for example. A spring 7 arranged on the far side of the articulation 5 in relation to the cylinder 6 allows to damp the pivoting movement of the inspection device.

A displacement of the piston of the cylinder 6 causes a pivoting of the inspection device about the axis of the bearings 5 and consequently a modification of the inclination of the optical axis of the inspection device. This modification is adapted in such a way as to ensure specular reflection at the surface of a new roll (not shown) replacing the current roll 4.

Figure 2:
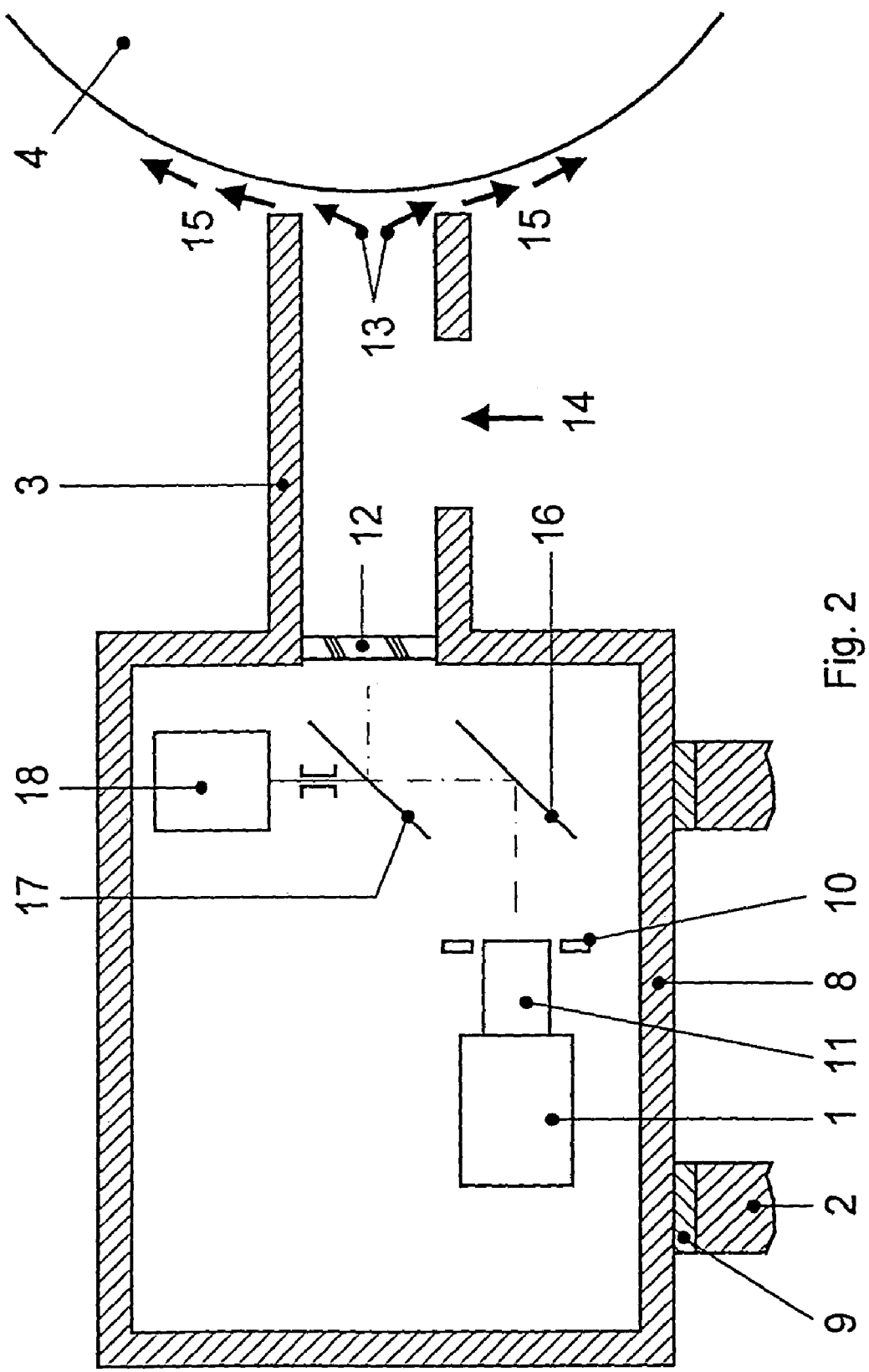
FIG. 2 represents a sectional view of an embodiment of an optical device for adjusting the inclination and/or position of the optical axis of an inspection device.

FIG. 2 represents an optical device for adjusting the position and/or the inclination of the optical axis of an inspection device.

Here, the camera 1 is mounted in a sealed housing 8, which is in turn mounted on a fixed support 2, possibly via vibration dampers 9. In a known manner, the objective 11 of the camera 1 is provided with a light source 10, and its optical axis is directed towards the roll 4.

On the same side as the roll 4, the housing 8 has an aiming cap 3 communicating with the inside of the housing 8 by a window 12 provided in the wall of the housing. This cap 3 extends to within a short distance of the roll 4, forming an end slit 13. There is a laminar flow 14, 15 of water through the cap 3, ensuring, on the one hand, that the window 12 is clean and ensuring, on the other hand, protection against penetration of particles through the slit 13. A clear and undisturbed view of the surface of the roll is thus guaranteed.

Within the housing 8, a first, fixed mirror 16 arranged opposite the objective 11 deviates the optical axis towards a second, pivoting mirror 17 placed at the level of the window 12. This second mirror 17 deviates the optical axis through the window 12 in the direction of the cylinder 4. The rotation of this second mirror 17, which is controlled by a galvanometer 18, allows to modify the final orientation of the optical axis to ensure specular reflection on the roll 4 when the diameter of the latter changes.

The size of the adjustment to be made to the inclination of the optical axis depends on the difference between the observed reflection and the optimum reflection, which is ideally specular, at the point of observation. In practice, the point of observation is located in the middle of a small zone observed on the surface of the roll. The image of this observed zone is captured and advantageously recorded by the camera 1.

In order to determine the correct position of the optical axis, the following procedure may be adopted.

Having adjusted the focus of the lens and possibly the illumination of the surface to be inspected, the inclination of the optical axis is progressively modified and, for each position of said optical axis, the image of the zone observed is recorded. For each image, the transverse profile of the average grey levels of each scanning line of the image is drawn. Finally, the inclination of the optical axis is adjusted to the angular position for which the selected characteristic size of this profile, e.g. the maximum or the centre of gravity, is located in the middle of the image of the zone observed.

Figure 3:
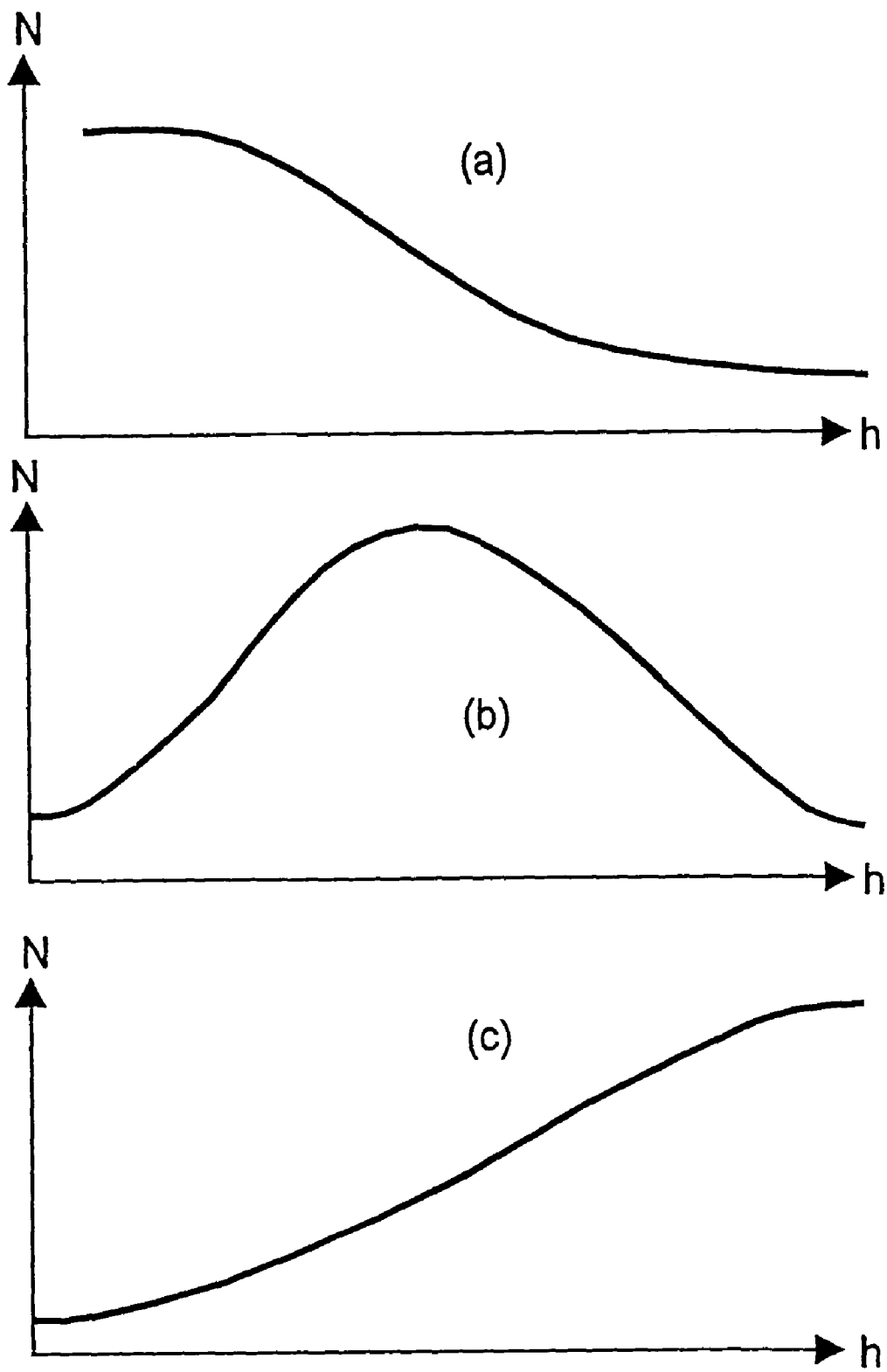
FIG. 3 shows three examples of transverse profiles of average grey levels in the sense of the present invention.

FIG. 3 shows examples of profiles of this average grey level.

The curves (a), (b) and (c) indicate the evolution of the average grey levels N of the lines corresponding to images, as a function of the position h of the line in the image, considered in a direction perpendicular to said lines and counted from the bottom of the image.

The curves (a) and (c) respectively indicate that the best reflection is achieved in the bottom part and in the top part, respectively of the zone observed. The corresponding inclinations do not allow satisfactory observation of the surface of the roll 4. On the other hand, the curve (b) expresses specular reflection in the central region of the zone observed, i.e. good distribution of the field of observation in this zone.

The optical axis will therefore ideally be positioned at this inclination. A mechanical device or an optical device of the above-described type could be used to this end, for example.

In the above description, it was tacitly assumed that the optical axis of the inspection device was situated in a plane perpendicular to the axis of the cylindrical body and, more especially to the axis of the mill roll. However, this is not an obligatory or restrictive condition, and the invention likewise extends to the adjustment of said optical axis with respect to another axis, to correct a defect of perpendicularity of said plane with respect to the axis of the cylindrical body for example.

What is claimed is:

1. A process for the inspection of the surface of a cylindrical body, in which
   at least one zone of said surface is observed by means of an inspection device having an optical axis oriented towards said zone in order to determine the condition of the surface,
   one image of said zone supplied by said inspection device is captured and analyzed, the analysis of said image captured being compared with the analysis of a reference image, the differences between the analysis of the image captured and the analysis of said reference image being detected,
   at least the orientation of said optical axis is adjusted so as to reduce or to eliminate said differences, wherein
   the orientation of the optical axis of the inspection device directed towards the zone of the surface to be inspected is progressively varied and adjusted,
   said zone is observed for each position of said optical axis by scanning parallel to the direction of the cylindrical body axis,
   an image of said zone, comprising lines parallel to the direction of the cylindrical body axis is formed,
   the average value of the grey level of each of said lines of the image is determined,
   a profile of said average grey levels is drawn,
   each of said profiles drawn is compared with a reference profile corresponding to a correct inclination of the optical axis, and
   the inclination of the optical axis is modified in order to correct any differences observed between said profiles drawn and said reference profile.

2. The process according to claim 1, wherein, in the step of comparison of the profiles drawn with a reference profile corresponding to a correct inclination of the optical axis, the position of a characteristic size of the profile corresponding to each image is determined, and the inclination of the optical axis is adjusted to the optical axis position so that the position of said characteristic size of said profile is equal to or close to the position of the characteristic size corresponding to an image for which the reflection is specular at the center of the image.

3. The process according to claim 2, wherein the characteristic size of said profile is selected from the group consisting of the maximum and the center of gravity of said profile.

4. The process according to claim 1, wherein the average grey level of a line of the image is determined by measuring the grey level at a predetermined number of points, and by calculating the average value of the grey levels measured at these points of the line.

5. The process according to claim 1, wherein the cylindrical body is a mill roll.

6. The process according to claim 1, wherein the inclination of the optical axis is measured and displayed.

7. The process according to claim 1, wherein a focusing of the inspection device is adjusted.

8. The process according to claim 1, wherein illumination of the zone of the surface to be inspected and the sensitivity of the inspection device are adjusted.

* * * * *